(12) United States Patent
Georgescu et al.

(10) Patent No.: US 7,755,489 B2
(45) Date of Patent: Jul. 13, 2010

(54) INTELLIGENT PACKAGING METHOD AND SYSTEM BASED ON ACOUSTIC WAVE DEVICES

(75) Inventors: Ion Georgescu, Bucharest (RO); Cornel Cobianu, Bucharest (RO); Viorel-Georgel Dumitru, Prahova (RO)

(73) Assignee: Honeywell International Inc., Morristown, NJ (US)

( * ) Notice: Subject to any disclaimer, the term of this patent is extended or adjusted under 35 U.S.C. 154(b) by 285 days.

(21) Appl. No.: 12/110,948

(22) Filed: Apr. 28, 2008

(65) Prior Publication Data

US 2009/0267761 A1 Oct. 29, 2009

(51) Int. Cl.
*G08B 13/14* (2006.01)

(52) U.S. Cl. .............. 340/572.1; 340/572.2; 340/572.4; 340/10.1; 333/150; 333/154; 333/193; 333/195

(58) Field of Classification Search ... 340/572.1–572.8, 340/10.1, 825.71, 825.72; 333/150, 154, 333/193, 195
See application file for complete search history.

(56) References Cited

U.S. PATENT DOCUMENTS

| | | | | |
|---|---|---|---|---|
| 5,285,734 A * | 2/1994 | MacPherson | ................. | 109/42 |
| 5,506,566 A * | 4/1996 | Oldfield et al. | ............. | 340/550 |
| 6,010,771 A | 1/2000 | Isen et al. | .................... | 428/209 |
| 6,050,622 A * | 4/2000 | Gustafson | ................ | 292/307 R |
| 6,084,503 A | 7/2000 | Ruile et al. | ................. | 340/10.1 |
| 6,107,920 A * | 8/2000 | Eberhardt et al. | ........ | 340/572.7 |
| 6,144,288 A * | 11/2000 | Jahn et al. | ................. | 340/10.33 |
| 6,244,462 B1 | 6/2001 | Ehrensvard et al. | ............ | 221/7 |
| 6,259,369 B1 * | 7/2001 | Monico | .................... | 340/572.8 |
| 6,515,587 B2 * | 2/2003 | Herbert | ...................... | 340/550 |
| 6,703,935 B1 * | 3/2004 | Chung et al. | ............. | 340/572.7 |
| 6,788,204 B1 * | 9/2004 | Ianelli et al. | ............. | 340/572.1 |
| 6,888,509 B2 | 5/2005 | Atherton | ..................... | 343/718 |
| 7,005,987 B2 * | 2/2006 | Sinnett et al. | ............ | 340/572.1 |
| 7,089,786 B2 | 8/2006 | Walker | .......................... | 73/73 |
| 7,170,409 B2 * | 1/2007 | Ehrensvard et al. | .... | 340/539.26 |
| 7,259,676 B2 * | 8/2007 | Knadle et al. | ............. | 340/572.4 |
| 7,301,460 B2 * | 11/2007 | Coste | ...................... | 340/572.7 |
| 2002/0186145 A1 | 12/2002 | Chainer et al. | ......... | 340/870.16 |
| 2005/0011163 A1 | 1/2005 | Ehrensvard et al. | ........... | 53/410 |
| 2005/0145629 A1 | 7/2005 | Herr | .......................... | 220/293 |
| 2005/0187089 A1 | 8/2005 | Schneider et al. | .......... | 493/394 |
| 2005/0242957 A1 | 11/2005 | Lindsay et al. | ........... | 340/572.7 |
| 2005/0280512 A1 * | 12/2005 | Forster | .................... | 340/10.34 |
| 2006/0220855 A1 | 10/2006 | Hartmann et al. | ........ | 340/572.1 |
| 2008/0001741 A1 | 1/2008 | Cobianu et al. | .......... | 340/568.2 |
| 2009/0284351 A1 * | 11/2009 | Rossman et al. | ........... | 340/10.1 |

FOREIGN PATENT DOCUMENTS

| WO | WO 02/058080 A1 | 7/2002 |
|---|---|---|
| WO | WO 2005/081157 A1 | 9/2005 |
| WO | WO 2006/016343 A1 | 2/2006 |

* cited by examiner

*Primary Examiner*—Daniel Wu
*Assistant Examiner*—Son M Tang

(57) ABSTRACT

An intelligent packaging system utilizing acoustic wave devices includes an electronic module, a SAW ID, various passive SAW sensors and a printed antenna. The passive SAW sensors include a SAW pressure sensor, a SAW temperature sensor and one or more SAW chemical sensors for monitoring physical parameters of a package content. The electronic module generally includes a printed large area distributed electrical circuit, an impedance transformer and a SAW transponder for realizing passive wireless monitoring of the structural integrity of the package. A separate power harvesting antenna and/or a separate dual band antenna can generate radio frequency (RF) power for biasing components associated with the electronic module.

20 Claims, 5 Drawing Sheets

INTELLIGENT PACKAGING METHOD AND SYSTEM BASED ON ACOUSTIC WAVE DEVICES

TECHNICAL FIELD

Embodiments are generally related to techniques for the intelligent packaging of goods. Embodiments are also related to surface acoustic wave (SAW) devices. Embodiments are additionally related to the packaging of electronic devices utilizing SAW-based components.

BACKGROUND OF THE INVENTION

Innovative packaging systems with enhanced functions are constantly sought in response to consumer, producer, and government demands. So-called "intelligent" packaging can be thought of as packaging techniques capable of carrying out intelligent functions (e.g., detecting, sensing, recording, tracing, communicating, and applying scientific logic) to facilitate decision making, extending shelf life, enhancing safety, improving quality, providing information, and warning about possible problems. Intelligent packaging systems typically include internal or external sensors for monitoring external conditions (e.g., temperature) or indicator compounds (e.g., volatiles) associated with the packaged goods that can indicate a quality status. Such sensors can be linked to, for example, RFID-tags that communicate sensor information during the entire supply chain.

The quality of packaged goods can vary considerably during shelf life. Hence, passive wireless monitoring of such packaged goods during transportation and storage in a logistic chain is highly desirable. Monitoring quality during transport and storage in the production chain provides additional information for the enhanced prediction of product quality, while also providing important information for logistic control of the supply chain. Also, package-tampering events, illegal opening as well as other parameters such as, for example, temperature, pressure, humidity or chemical composition change endured by the packaged goods during shipment and storage, should be monitored.

Prior art package monitoring approaches have been implemented, which ensure the integrity of packages during shipment utilizing different types of sealing, so that a tamper event can be visually detected at the time of arrival. More advanced systems incorporate the use of, for example, "smart" RFID tags for recording the history of the package, tracking the time of a tamper event, and monitoring other parameters such as temperature, pressure or humidity endured by the package during shipment. Such approaches, however, address either small dimensional objects or do not suitably monitor the entire area of the package in order to allow the detection of any rupture with a specific size.

Other prior art monitoring approaches have been utilized, which include wireless monitoring of tampering events. Wireless components utilized in such scenarios are suitable to be employed within or associated with pallets and containers having large dimensions. Such systems, however, are not passive in nature and often require a battery for proper operation. Such an approach is not suitable for providing passive wireless monitoring of the structural integrity of the package and also the physical properties of the package content, particularly in the case of large dimensional packages and containers. Therefore, for widespread use of a smart packaging approach, a low cost and efficient solution is required. It is believed that such a solution should be based on passive sensors and battery-less RFID components, which are capable of providing wireless monitoring of the structural integrity of packages including large dimensional packages. Additionally, an improved technique and/or system are needed for monitoring various physical and chemical parameters of a package content. Such an improved "intelligent" packaging method and system is described in greater detail herein.

BRIEF SUMMARY

The following summary is provided to facilitate an understanding of some of the innovative features unique to the embodiments disclosed and is not intended to be a full description. A full appreciation of the various aspects of the embodiments can be gained by taking the entire specification, claims, drawings, and abstract as a whole.

It is, therefore, one aspect of the present invention to provide for an improved intelligent packaging method and system.

It is another aspect of the present invention to provide for an improved method and system for passive wireless monitoring of packages and containers utilizing acoustic wave devices, such as, for example SAW (Surface Acoustic Wave) based components.

It is a further aspect of the present invention to provide for an improved method and system for monitoring various physical and chemical parameters of the contents of a package during transport and storage, and additionally throughout a supply chain.

The aforementioned aspects and other objectives and advantages can now be achieved as described herein. An intelligent packaging system is disclosed, which includes the use of an electronic module, a SAW identification (ID) component, various passive SAW sensors and a printed antenna. The passive SAW sensors include, for example, a SAW pressure sensor, a SAW temperature sensor and one or more SAW chemical sensors for monitoring physical parameters of a package content. The electronic module generally includes a printed large area distributed electrical circuit, such as, for example, a Wheatstone bridge circuit. The electronic module can further include the use of an impedance transformer and a SAW transponder for realizing passive wireless monitoring of the structural integrity of the package. A separate power harvesting antenna and/or a separate dual band antenna can be utilized to generate radio frequency (RF) power for biasing components associated with the electronic module.

The distributed electrical circuit can be printed on a dielectric film for wrapping pallets or containers in a logistic chain, wherein the distributed electrical circuit (e.g., the Wheatstone bridge) can be employed to detect a rupture of the film via an electrical resistance change of one or more elements of the distributed electrical circuit. The electrical resistance change is indicative of a potential tampering event. The impedance transformer possesses a high input impedance and a low output impedance in order to influence a SAW inter-digital transducer (IDT) for signal functioning. Such an impedance transformer generally includes a rectifier, a signal conditioner and a driver.

The resistance range of a distributed resistor associated with the large area distributed Wheatstone bridge can be increased to very large values as the differential voltage signal offered by the distributed electrical circuit is connected to a high input impedance operational amplifier. Such large resistance values associated with the printed distributed resistor can allow low-cost, high spatial resolution monitoring of packages including packages having large dimensions. The power needed for biasing the distributed electrical circuit, the signal conditioner and the driver can be obtained from RF power generated by a SAW IDT for batteryless operation. The RF power can also be obtained from the power harvesting antenna and/or the separate dual band antenna.

BRIEF DESCRIPTION OF THE DRAWINGS

The accompanying figures, in which like reference numerals refer to identical or functionally-similar elements throughout the separate views and which are incorporated in and form a part of the specification, further illustrate the embodiments and, together with the detailed description, serve to explain the embodiments disclosed herein.

DETAILED DESCRIPTION

The particular values and configurations discussed in these non-limiting examples can be varied and are cited merely to illustrate at least one embodiment and are not intended to limit the scope thereof.

Figure 1:
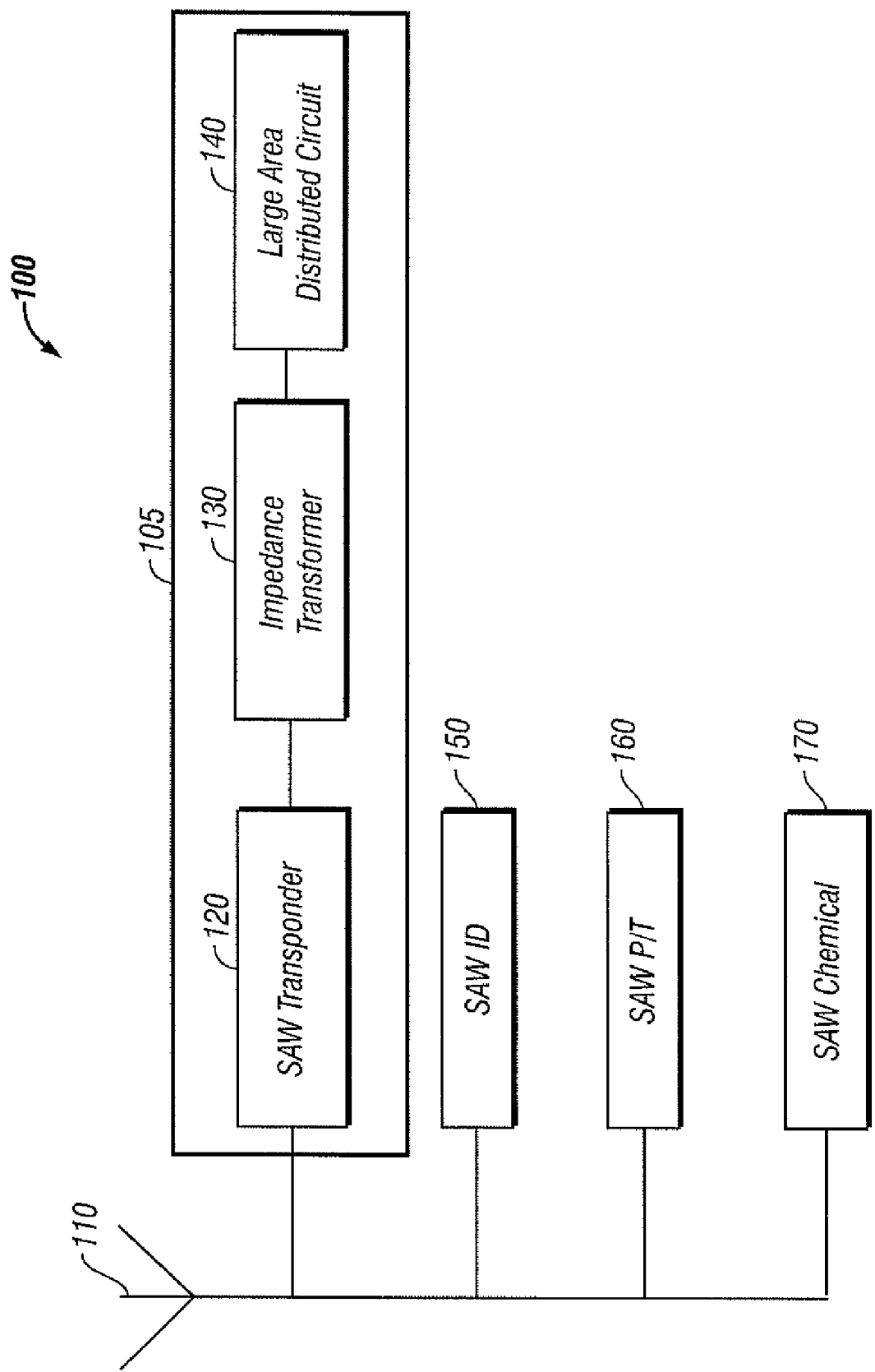
FIG. 1 illustrates a block diagram of an intelligent packaging system utilized for passive wireless monitoring of packages and containers, which can be implemented in accordance with an preferred embodiment.

FIG. 1 illustrates a block diagram of an intelligent packaging system 100 for passive wireless monitoring of packages and containers, which can be implemented in accordance with a preferred embodiment. The intelligent packaging system 100 includes an electronic module 105, a SAW identification (ID) 150, SAW sensors 160 and 170 and a printed antenna 110. The electronics module 105 typically includes a large area distributed electrical circuit 140, a SAW transponder 120 and an impedance transformer 130. The various passive SAW sensors 160 and 170 realize real time monitoring of physical parameters of a package content. The SAW sensors include a SAW pressure sensor 160 for monitoring the pressure inside a hermetically or vacuum closed package, a SAW temperature sensor 160 for monitoring the temperature of the package and one or more SAW chemical sensor 170 for monitoring chemical composition inside the package.

Figure 2:
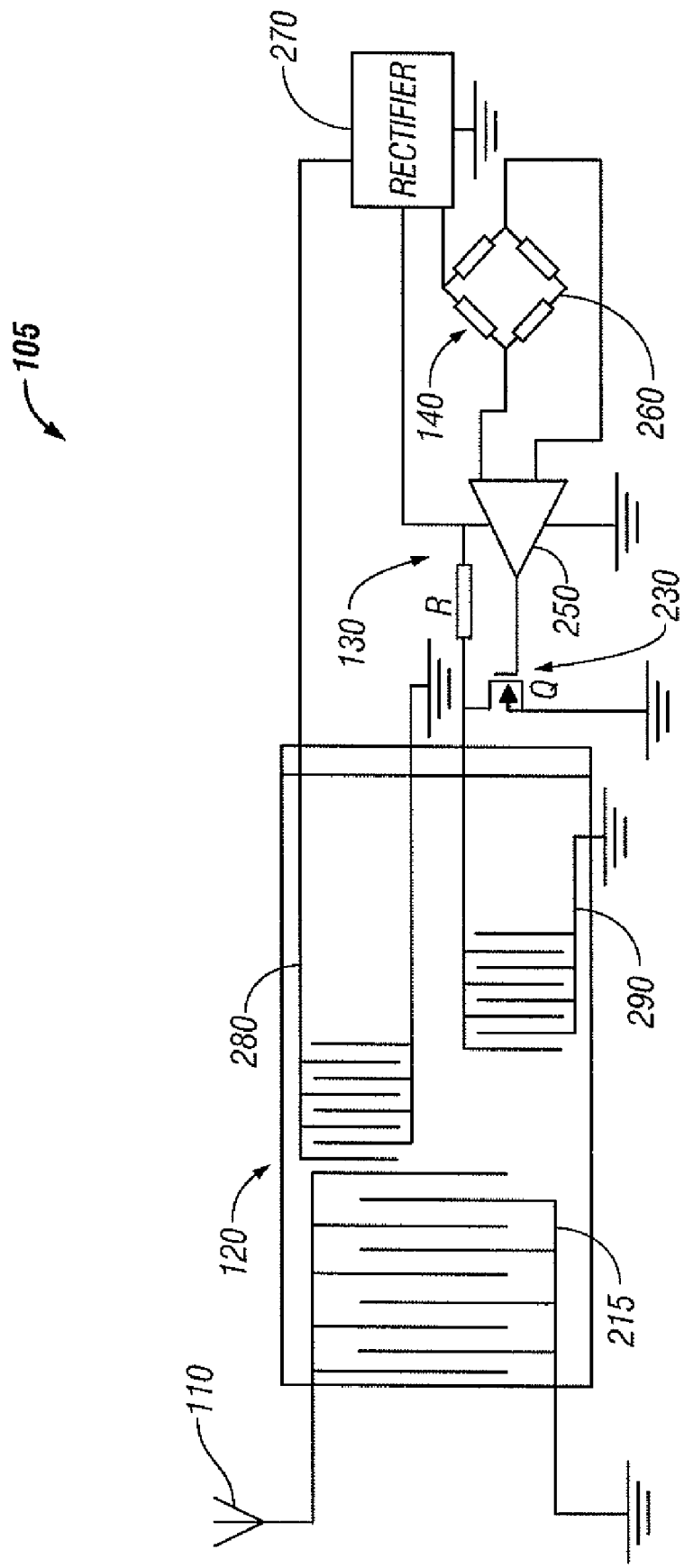
FIG. 2 illustrates a schematic diagram of an electronic module, and a SAW antenna for passive wireless monitoring of packages and containers, which can be implemented in accordance with an preferred embodiment.

The impedance transformer 130 connects the SAW transponder 120 with the large area distributed circuit 140, which comprises a Wheatstone bridge 260, as shown in FIG. 2. The printed large area distributed electrical circuit 140 together with the impedance transformer 130 and the SAW transponder 120 realize the passive wireless monitoring of the structural integrity of the package. The antenna 110, as indicated in FIG. 1, can be utilized for wirelessly transmitting the signals. The impedance transformer 130 possesses a high input impedance and a low output impedance. The SAW ID 150 includes a piezoelectric material and an identification transducer (not shown) which includes a metallic interdigital transducer (IDT) and a number of metal reflectors all preformed on the piezoelectric material, where the number and spatial distribution of the reflectors can be used for the ID of that package, such as the SAW ID discussed herein. The SAW ID 150 receives a radio frequency signal and propagates a corresponding surface acoustic wave along the surface of the piezoelectric material to the group of reflectors. The reflected mechanical signal can possess a shape depending on the number of reflectors, which can be then converted back into an electrical signal for transmission back to the electronic interrogator of the "echo" signal containing the ID information of that monitored package or container.

FIG. 2 illustrates a schematic diagram of the electronic module 105 depicted in FIG. 1, comprising the SAW transponder 120, the impedance transformer 130, the large area distributed circuit 140 and a SAW antenna 110 for monitoring the structural integrity of packages and containers, in accordance with a preferred embodiment. Note that in FIGS. 1-5, identical or similar blocks are generally indicated by identical reference numerals. The SAW transponder 120 generally includes three interdigital transducers: an input IDT 215 connected to the antenna 110, a reference IDT 280 and a sensing IDT 290. The IDT 280 can function both as an energy harvester and as a reference IDT that together with the sensing IDT 290, provide a differential measurement. The electronic interrogator (not described herein) can receive the signal from the reference IDT and the sensing IDT 290 and a noise-free difference signal can be obtained at the output of that interrogator in order to provide information about a potential tampering event.

The SAW transponder 120 can be connected through the impedance transformer 130 with the printed large area distributed electrical circuit 140 (e.g., Wheatstone bridge configuration 260, which can also function as a signal conditioning circuit) for monitoring the structural integrity of a dielectric film (e.g., see dielectric film 510 in FIG. 5) wrapping the package or container. The large area distributed electrical circuit 140 can be printed on a dielectric film 510, which can be utilized for wrapping packages, pallets or containers. The large area distributed electrical circuit 140 can be utilized to detect a rupture of the dielectric film 510 through an electrical resistance change of one or more elements of the (i.e. large area) distributed electrical circuit 140.

The impedance transformer 130 includes a rectifier 270, a signal processing unit 250 and a MOSFET-type driver 230. The signal from the impedance transformer 130 can be fed to a sensing IDT 290. The signal-processing unit 250 can be provided as an instrumentation amplifier including one or more operational amplifiers (not shown herein), which can be utilized to process the differential voltage signal offered by the Wheatstone bridge 260 due to a tampering event conducting to electrical resistance change of the elements associated with the Wheatstone bridge 260. The signal processing unit 250 has a high input impedance such as not to influence the functioning of the Wheatstone bridge 260.

The driver 230 from the composition of the impedance transformer 130 possesses a low output impedance that can influence the sensing IDT 290 for signal functioning. RF electric power can be generated by the reference IDT 280 (by a piezoelectric effect) for biasing the Wheatstone bridge 260, the signal processing unit 250 and the driver 230. The rectifier 270 transforms the RF electric power into a DC power, which can be utilized for biasing the Wheatstone bridge 260, the signal processing unit 250 and the driver 230. The signal processing unit 250 receives the differential voltage signal offered by the Wheatstone bridge 260 and sends a voltage signal to the driver 230. The driver 230 includes a FET Q and a resistor R, as indicated in FIG. 2. The resistor R possess a high resistance value such as not to influence the SAW sensing IDT 290 for signal. The SAW sensing IDT 290 for signal can be loaded only by the resistor R, when the FET Q is in OFF state. The energy harvester SAW IDT 280 can be utilized also as a reference IDT because it can reflect some of the mechanical energy back to the input IDT 215 in substantially the same manner, regardless of whether the FET Q is in an OFF or an ON state.

The FET Q turns ON as a result of the voltage signal given by the signal processing unit 250 due to a tamper event detected by the large area distributed Wheatstone bridge 260. When FET Q is in ON state the load resistance value on the SAW sensing IDT 290 for signal is significantly changed and consequently the response signal from the SAW sensing IDT 290 is also changed. Therefore the SAW transponder 120 possesses a different response for the situation, when a tampering event is occurred. The power needed for biasing the Wheatstone bridge 260, the signal processing unit 250 and the driver 230 can be provided by the reference IDT 280 and the SAW antenna 110.

Figure 3:
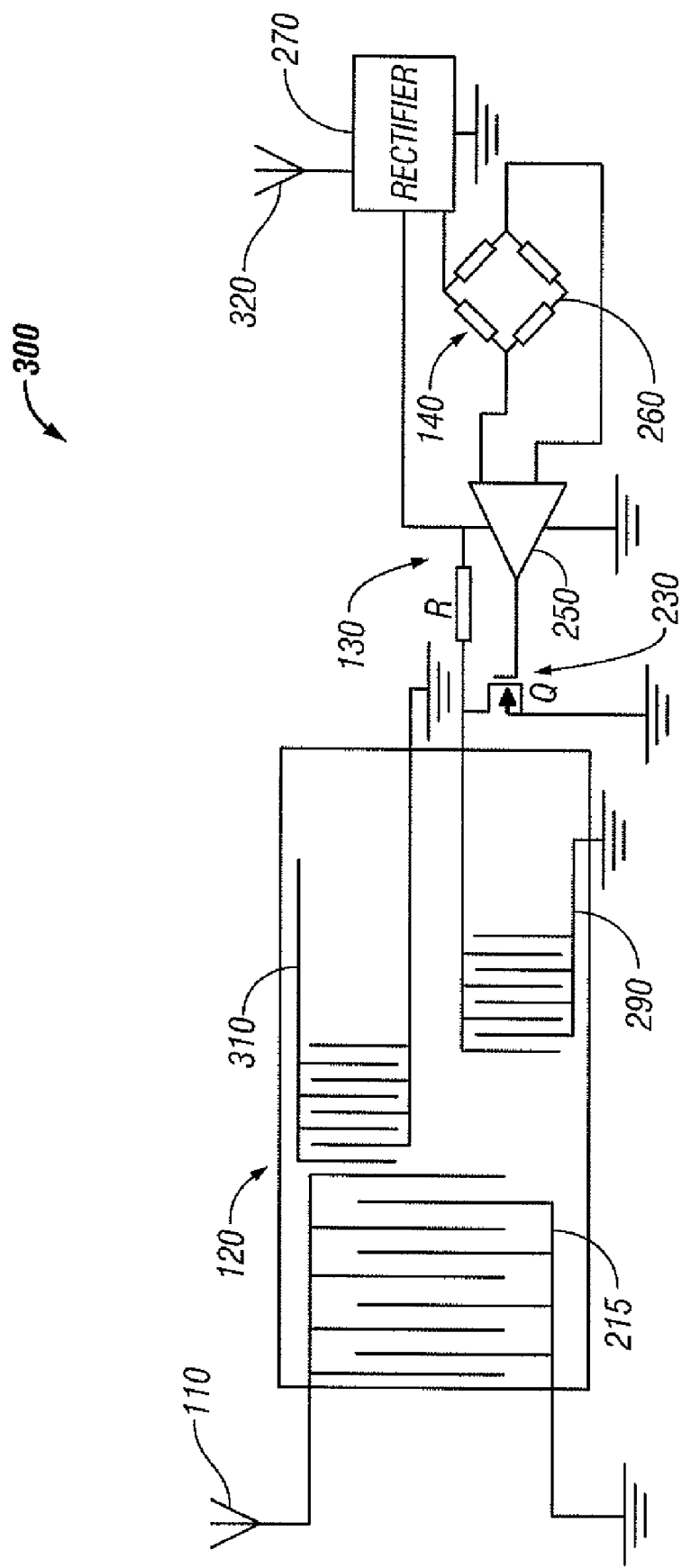
FIG. 3 illustrates a schematic diagram of the electronic module with a power harvesting antenna for generating power needed for biasing the electronic components, which can be implemented in accordance with an alternative embodiment.

FIG. 3 illustrates a schematic diagram of a circuit 300 of the electronic module 105 associated with a power-harvesting antenna 320 for generating electric power needed for biasing the electronic components, in accordance with an alternative embodiment. As indicated in the illustration of FIG. 3, the power-harvesting antenna 320 can be utilized for biasing the Wheatstone bridge 260, the signal processing unit 250 and the driver 230. The power-harvesting antenna 320 utilizes the same frequency band as the SAW antenna 110 or a different frequency band. In this case the IDT 310 acts only as a reference IDT for allowing together with the sensing IDT 290, a differential measurement.

Figure 4:
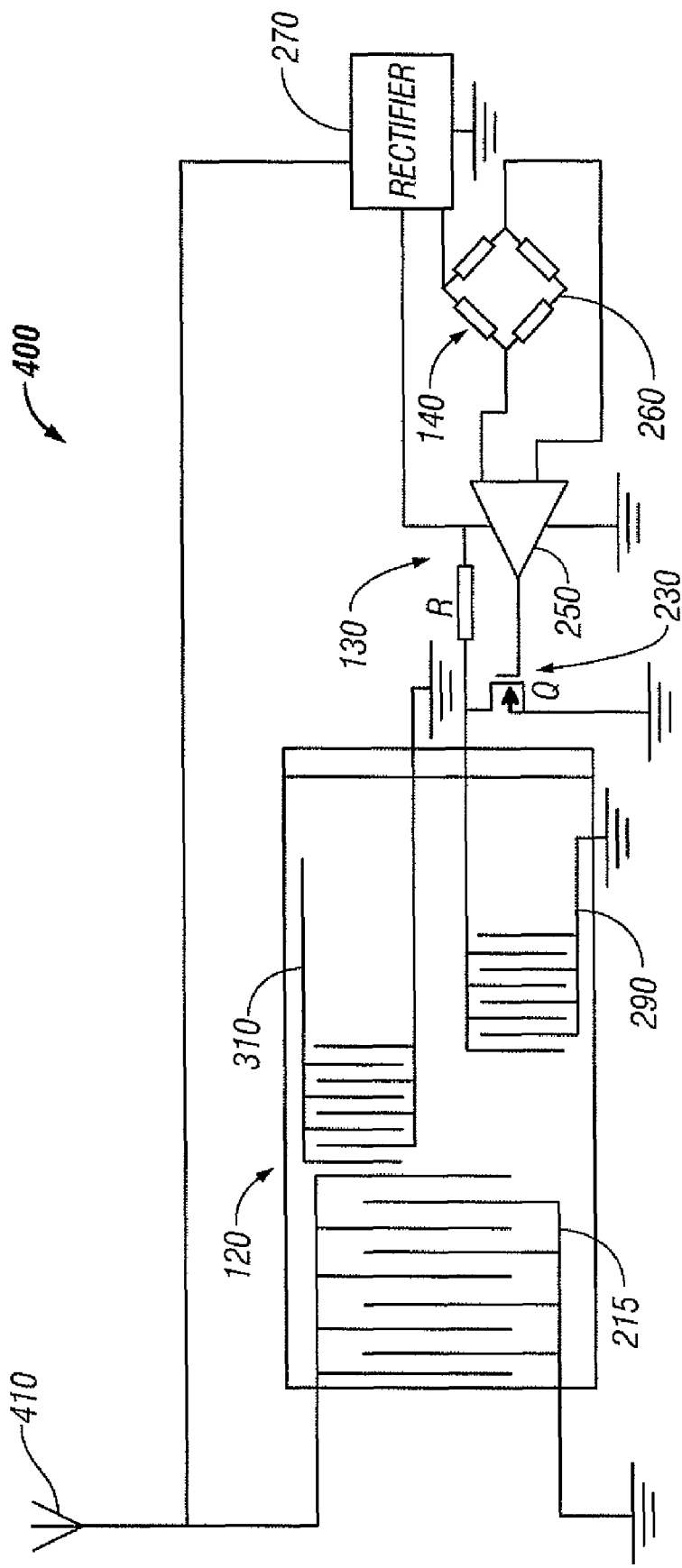
FIG. 4 illustrates a schematic diagram of the electronic module with a dual band antenna for power harvesting, which can be implemented in accordance with an alternative embodiment.

FIG. 4 illustrates a schematic diagram of a circuit 400 of the electronic module 105 with a multifunctional dual band antenna 410, which can be implemented in accordance with an alternative embodiment. The dual band antenna 410 can be utilized for SAW interrogation and power harvesting. One frequency band of the dual band antenna 410 can be utilized for the SAW interrogation and the other frequency band of the dual band antenna 410 is for power harvesting the impedance transformer 130. The dual band antenna 410 can be printed on the dielectric film 510 utilized for wrapping packages or containers. In this case, the IDT 310 can function only as a reference IDT for allowing together with the sensing IDT 290, a differential measurement.

Figure 5:
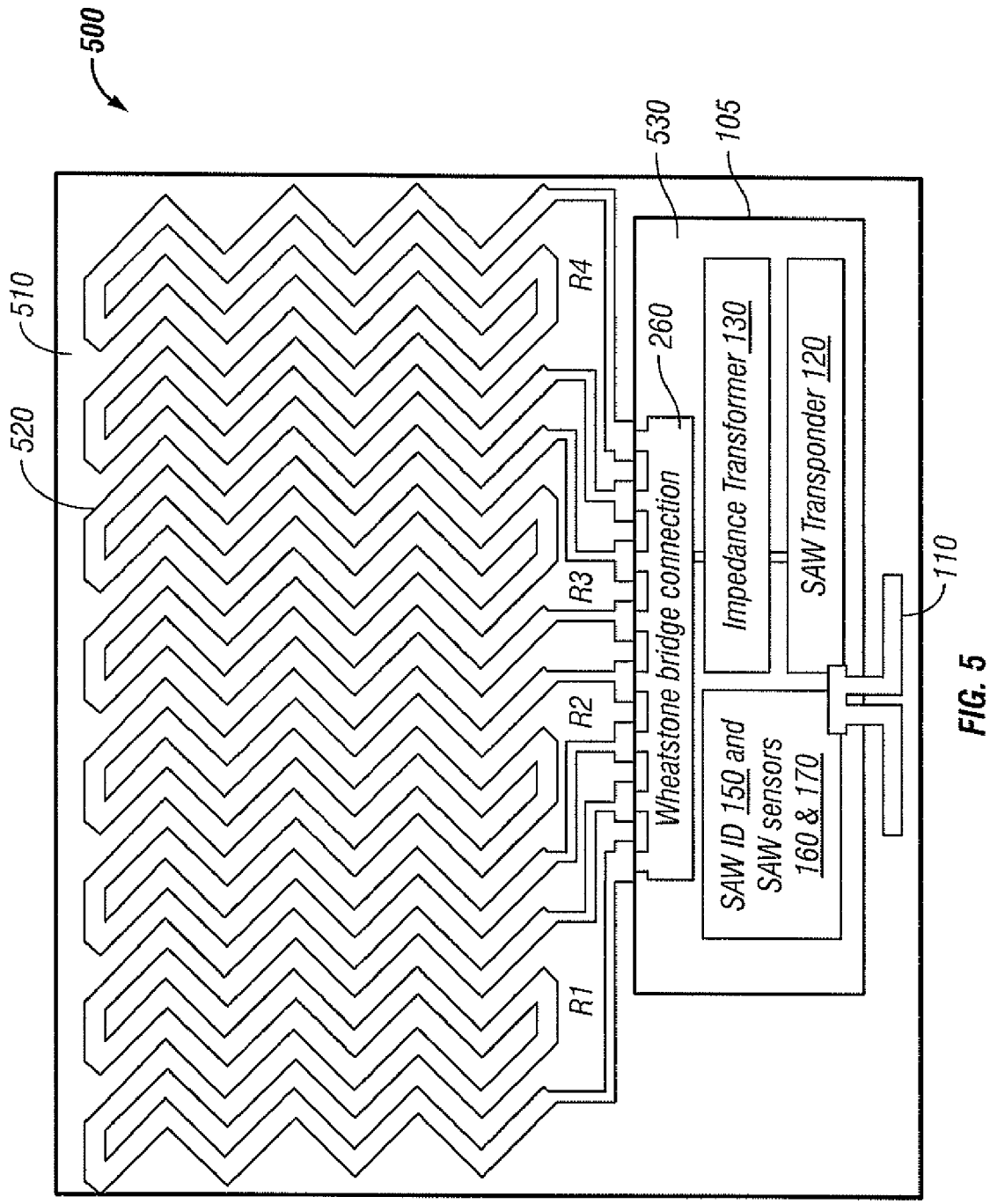
FIG. 5 illustrates a schematic diagram of the intelligent packaging system utilized for passive wireless monitoring of packages and containers, which can be implemented in accordance with a preferred embodiment.

FIG. 5 illustrates a schematic diagram of the intelligent packaging system 500 for passive wireless monitoring of packages and containers, which can be implemented in accordance with a preferred embodiment. Again, as a reminder, in FIGS. 1-5, identical or similar elements and components are generally indicated by identical reference numerals. The intelligent package system 500 includes a PCB (Printed Circuit Board) layout 530 and a SAW antenna 110 printed on the printed circuit board layout 530. The PCB 530 generally includes, for example, the use of SAW devices such as the SAW ID 150, the SAW pressure and temperature sensor 160, the SAW chemical sensor 170 and the impedance transformer 130. The intelligent package system 500 further includes electrically printed conductive traces 520 that can be printed on a dielectric film 510 utilized for package wrapping either before or after the wrapping process by different printing technologies.

For this purpose, an electrically conductive ink can be printed by screen-printing, flexography, ink-jet or other printing technologies. In case the printed electrically conductive traces 520 can be realized after wrapping, ink-jet printing technology can be preferably utilized. When the conductive traces 520 are printed before the wrapping process, large area printing technologies such as screen printing or flexography can be preferably utilized. Various conductive inks such as, for example, metallic nanoparticle based inks, inherently conductive polymers and/or metal-filled polymer based inks, can be adapted for use in printing the electrically conductive traces 520. It can be appreciated that other types of printing technologies and conductive inks may also be utilized depending upon design considerations.

The SAW antenna 110 can be printed on the dielectric film 510 for wrapping packages or containers or can be attached onto it. The SAW reference IDT 280, the power-harvesting antenna 320 (not shown in FIG. 5) and the dual band antenna 410 (not shown in FIG. 5) can also be printed on the dielectric film 510 for power harvesting. The passive SAW sensors 160 and 170 together with the SAW transponder 120, the SAW ID 150 and the impedance transformer 130 can be placed on the PCB 530 that is attached on the dielectric film 510 inside the package and is connected via s-type contacts with the printed large area distributed circuit 140.

A rupture may appear in the dielectric film 510 during a tampering event, which also indicates the interruption of the conductive trace 520, thereby changing the electrical resistance of one arm of Wheatstone bridge circuit 260. The electronic module 105 can be utilized to process the signal from the large area distributed Wheatstone bridge circuit 260 and detect the event. The concerning event signals can be wirelessly transmitted through the antenna 110 to a real-time monitoring station (not shown).

The resistance range of a constituent distributed resistor R1, R2, R3, and R4 associated with the large area distributed Wheatstone bridge 260 can be increased to very large values as the differential voltage signal offered by the Wheatstone bridge 260 can be connected to a high input impedance signal processing unit 250. Such very large values of resistance of the printed distributed resistor R1, R2, R3, and R4 allow for the low-cost, high spatial resolution monitoring of packages inclusive of those having large dimensions ones.

Additionally, the four large area distributed resistances R1, R2, R3, and R4 can be provided of equal value with respect to one another and configured from the same material and technology. Such a configuration generally results in the temperature and aging process influencing in the same manner, all the resistances and the differential operation of the Wheatstone bridge 260, which may cancel the affect of aging/drift on the tampering event detection. The intelligent package system 500 provides a robust solution for tampering detection, which is insensitive to temperature and aging/drift phenomena in the conductive traces 520. Such a packaging system 500 provides a low-cost solution for passive wireless monitoring of the structural integrity of packages and containers including those having large dimensions, while also monitoring various physical and chemical parameters associated with the package content.

It will be appreciated that variations of the above-disclosed and other features and functions, or alternatives thereof, may be desirably combined into many other different systems or applications. Also, that various presently unforeseen or unanticipated alternatives, modifications, variations or improvements therein may be subsequently made by those skilled in the art which are also intended to be encompassed by the following claims.

What is claimed is:

1. An intelligent package monitoring system, comprising:
   an electronic module for tamper monitoring and identification of a package, said electronic module including a distributed electrical circuit printed on a dielectric film capable of being wrapped about said package in a logistic chain, wherein said distributed electrical circuit detects a rupture of said dielectric film through an electrical resistance change of at least one element of said distributed electrical circuit;
   a plurality of passive acoustic wave sensors for package identification and monitoring at least one physical parameter of said package content, said plurality of passive acoustic wave sensors capable of electronically communicating with an antenna for wirelessly transmitting a signal; and
   at least one acoustic wave interdigital transducer associated with said plurality of passive acoustic wave sensors and said electronic module, wherein said at least one acoustic wave interdigital transducer is capable of power harvesting in order to generate an RF power for biasing said electronic module, and thereby permitting a passive wireless monitoring of a structural integrity of said dielectric film and said package in said logistic chain thereto.

2. The system of claim 1 further comprising:
   an impedance transformer and an acoustic wave transponder in association with said electronic module in order to assist in said passive wireless monitoring of said structural integrity of said package.

3. The system of claim 1 wherein said distributed electrical circuit comprises a large area distributed Wheatstone bridge circuit comprising a plurality of bridge arms composed of printed electrically conductive traces.

4. The system of claim 1 further comprising a separate power-harvesting antenna for generating said RF power.

5. The system of claim 1 further comprising a dual band power-harvesting antenna for generating said RF power.

6. The system of claim 1 further comprising a rectifier, a signal processing unit and a driver in association with said impedance transformer.

7. The system of claim 1 wherein said plurality of passive acoustic wave sensors comprise at least one of the following:
   a SAW pressure sensor,
   a SAW temperature sensor,
   a SAW ID associated with said package; and
   a plurality of SAW chemical sensors for monitoring a pressure, a temperature and a chemical composition of said package content.

8. The method of claim 1 further comprising providing a separate power-harvesting antenna for generating said RF power.

9. The method of claim 1 further comprising providing a dual band power-harvesting antenna for generating said RF power.

10. The method of claim 1 further comprising providing a rectifier, a signal processing unit and a driver in association with said impedance transformer.

11. An intelligent package monitoring system, comprising:
    an electronic module for tamper monitoring and identification of a package, said electronic module including a distributed electrical circuit printed on a dielectric film capable of being wrapped about said package in a logistic chain, wherein said distributed electrical circuit detects a rupture of said dielectric film through an electrical resistance change of at least one element of said distributed electrical circuit;
    a plurality of passive acoustic wave sensors for package identification and monitoring at least one physical parameter of said package content, said plurality of passive acoustic wave sensors capable of electronically communicating with an antenna for wirelessly transmitting a signal;
    at least one acoustic wave interdigital transducer associated with said plurality of passive acoustic wave sensors and said electronic module, wherein said at least one acoustic wave interdigital transducer is capable of power harvesting in order to generate an RF power for biasing said electronic module, and thereby permitting a passive wireless monitoring of a structural integrity of said dielectric film and said package in said logistic chain thereto; and
    an impedance transformer and an acoustic wave transponder in association with said electronic module in order to assist in said passive wireless monitoring of said structural integrity of said package.

12. The system of claim 11 wherein said distributed electrical circuit comprises a large area distributed Wheatstone bridge circuit comprising a plurality of bridge arms composed of printed electrically conductive traces.

13. The system of claim 11 further comprising a separate power-harvesting antenna for generating said RF power.

14. The system of claim 11 further comprising a dual band power-harvesting antenna for generating said RF power.

15. The system of claim 11 further comprising a rectifier, a signal processing unit and a driver in association with said impedance transformer.

16. The system of claim 11 wherein said plurality of passive acoustic wave sensors comprise at least one of the following:
    a SAW pressure sensor;
    a SAW temperature sensor;
    a SAW ID; and
    a plurality of SAW chemical sensors for monitoring a pressure, a temperature and a chemical composition of said package content.

17. A method for monitoring a package, comprising:
    providing an electronic module for tamper monitoring of said package, said electronic module including a distributed electrical circuit printed on a dielectric film capable of being wrapped about said package in a logistic chain, wherein said distributed electrical circuit detects a rupture of said dielectric film through an electrical resistance change of at least one element of said distributed electrical circuit;
    associating a plurality of passive acoustic wave sensors with said electronic module, wherein said plurality of passive acoustic wave sensors is capable of monitoring at least one physical parameter of said package content, said plurality of passive acoustic wave sensors capable of electronically communicating with an antenna for wirelessly transmitting a signal; and
    associating at least one acoustic wave interdigital transducer with said plurality of passive acoustic wave sensors and said electronic module, wherein said at least one acoustic wave interdigital transducer is capable of power harvesting in order to generate an RF power for biasing said electronic module, and thereby permitting a passive wireless monitoring of a structural integrity of said dielectric film and said package in said logistic chain thereto.

18. The method of claim 17 further comprising providing an impedance transformer and an acoustic wave transponder in association with said electronic module in order to assist in said passive wireless monitoring of said structural integrity of said package.

19. The method of claim 17 further comprising configuring distributed electrical circuit to include a large area distributed Wheatstone bridge circuit comprising a plurality of bridge arms composed of printed electrically conductive traces.

20. The method of claim 17 further comprising configuring said plurality of passive acoustic wave sensors to include at least one of the following:
   a SAW pressure sensor;
   a SAW temperature sensor;
   a SAW ID; and
   a plurality of SAW chemical sensors for monitoring a pressure, a temperature and a chemical composition of said package content.

* * * * *